(12) United States Patent
Sabel et al.

(10) Patent No.: US 7,025,991 B2
(45) Date of Patent: Apr. 11, 2006

(54) DRUG TARGETING SYSTEM, METHOD OF ITS PREPARATION AND ITS USE

(75) Inventors: Bernhard A. Sabel, Berlin (DE); Ulrike Schroeder, Dodendorf (DE)

(73) Assignee: NanoDel Technologies GmbH, Magdeburg (DE)

( * ) Notice: Subject to any disclaimer, the term of this patent is extended or adjusted under 35 U.S.C. 154(b) by 0 days.

(21) Appl. No.: 09/445,439

(22) PCT Filed: Jun. 13, 1997

(86) PCT No.: PCT/EP97/03099

§ 371 (c)(1), (2), (4) Date: Feb. 23, 2000

(87) PCT Pub. No.: WO98/56361

PCT Pub. Date: Dec. 17, 1998

(65) Prior Publication Data

US 2002/0034474 A1 Mar. 21, 2002

(51) Int. Cl.
*A61K 9/50* (2006.01)

(52) U.S. Cl. .................................. 424/500; 424/501
(58) Field of Classification Search ................ 424/489, 424/490, 491, 493, 496, 497, 498, 499, 500, 424/501, 502, 1.25, 1.29, 9.32; 264/5, 7, 264/4.1, 4, 4.3, 4.7
See application file for complete search history.

(56) References Cited

U.S. PATENT DOCUMENTS

| 5,133,908 | A |   | 7/1992  | Stainmesse et al. |         |
|-----------|---|---|---------|-------------------|---------|
| 5,759,580 | A | * | 6/1998  | Jans et al.       | 424/489 |
| 5,837,221 | A | * | 11/1998 | Bernstein et al.  | 424/9.52|
| 6,117,454 | A |   | 9/2000  | Kreuter et al.    |         |

FOREIGN PATENT DOCUMENTS

| DE |    197 45 950 |   | 4/1999  |
|----|---------------|---|---------|
| EP |        330180 | * | 8/1989  |
| EP |        486959 | * | 5/1992  |
| FR |      261 2400 |   | 9/1988  |
| WO |      94/15590 | * | 7/1994  |
| WO |      95/22963 | * | 8/1995  |
| WO |   WO 98/56361 |   | 12/1998 |
| WO |   WO 00/74658 |   | 12/2000 |

OTHER PUBLICATIONS

Beck P. et al., Influence of polybutylcyanoacrylate nanoparticles . . . , J. Microencapslulation, vol. 10, No. 1, pp. 101–112, 1993.*

R. Reszka, et al., Journal of Pharmacology and Experimental Therapeutics, vol. 280, No. 1, pp. 232–237, "Body Distribution of Free Liposomal and Nanoparticle–Associated Mitoxantrone in B16–Melanoma–Bearing Mice", 1997. XP–002129865.

P. Couvreur, et al., Journal of Pharmaceutical Sciences, vol. 71, No. 7, pp. 790–7925, "Toxicity of Polyalkylcyanoacrylate Nanoparticles II: Doxorubicin–Loaded Nanoparticles", Jul. 1982. 1XP–000783921.

* cited by examiner

*Primary Examiner*—Michael Hartley
(74) *Attorney, Agent, or Firm*—Pabst Patent Group LLP (57) ABSTRACT

A composition and method of fabrication are presented with which nanoparticles may be used as a tool to deliver drugs to a specific target within or on a mammalian body. Specifically, by using stabilizers other than Dextran 70.000 during the polymerization process, according to the present invention, surfactants, which were deemed necessary coating material in the prior art, are no longer required. This is a significant simplification of the fabrication procedure. Many substances are useful as stabilizers, but the preferred stabilizers comprise Dextran 12.000 or polysorbate 85. In the present invention a drug is either incorporated into or adsorbed onto the stabilized nanoparticles. This drug/nanoparticle complex is then administered to the organism on any route such as by oral application, injection or inhalation, whereupon the drug exerts its effect at the desired site of pharmacological action. In a novel medical treatment process, the drug/nanoparticle complex may be administered preferably either by intravenous injection or by oral application. The resulting drug action, which does not occur or which occurs only to an insufficient extent when the drug is administered alone, shows that when linked to said nanoparticles drugs can reach a specific target within or on the mammalian body. The usefulness of the present invention as a universal approach to deliver any drug or diagnostic agent to a specific target within or on the mammalian body was demonstrated by experiments showing an unexpected transfer of the drug across the blood brain barrier.

1 Claim, 4 Drawing Sheets

DRUG TARGETING SYSTEM, METHOD OF ITS PREPARATION AND ITS USE

This application is a 371 of PCT/EP97/03099, filed Jun. 13, 1997.

BACKGROUND OF THE INVENTION

This invention relates to both targeting system and to a method of manufacturing such a drug targeting system. The invention also relates to a useful method of targeting and delivering drugs, diagnostics and other physiologically effective substances to a target within the mammalian body, for example to the nervous system. This work is motivated by the search of new technologies that enhance the capability to deliver physiologically effective substances like drugs or diagnostically useful agents to a desired target within the mammalian body, including delivering such substances across the blood brain barrier (bbb) which is a generally recognized problem in neuropharmacology.

In a previous patent application (Kreuter et al.; U.S. patent application Ser. No. 08/203,326 and PCT/EP 95/00724 corresponding to WO 95/22963) a novel method of delivering drugs across the blood brain barrier by using nanoparticles to which drugs are complexed (incorporated or adsorbed) and which are then surrounded by a coating made of an appropriate surfactant is taught. The present invention pertains to a similar approach. Particularly, nanosphere drug targeting systems can be obtained now which can achieve the same effect as demonstrated in the prior art description (Kreuter et al., loc. cit) but which can be manufactured by a significantly simplified fabrication method. The present invention teaches a drug targeting system, a method of improved and simplified fabrication and a method of use of such a drug targeting system in the medical field.

Here, nanoparticle fabrication involves the polymerization by using a stabilizer other than dextran 70.000 which allows for the first time that coating the nanoparticle-drug complex with a surfactant, which was deemed a requirement to achieve the desired effect in the prior art (Kreuter et al., loc. cit.) can be omitted. Thus, the present invention teaches a method and composition of nanoparticles which is significantly simplified over prior art drug targeting systems and their method of manufacture. This system allows any drug ("drug" as used herein includes any substance administrable for therapeutic and/or diagnostic purposes) to cross the blood brain barrier (bbb) in order to achieve one or more of the following benefits: reducing the dose of a drug or diagnostic, allowing drugs that normally do not cross the bbb to penetrate into the brain and reducing the peripheral side effects by increasing the relative amount of the drug reaching the brain.

DISCUSSION OF THE BACKGROUND

The above-referenced patent applications by Kreuter et al. (Kreuter et al., U.S. patent application Ser. No. 08/203,326 and PCT/EP 95/00724 corresponding to WO 95/22963) teach a method whereby nanoparticles may be utilized to help drugs and diagnostics to cross the blood brain barrier which is furtheron sometimes referred to shortly as "bbb". In this prior art, an appropriate monomer such as butyl cyanoacrylate (BCA) is selected and polymerized to polybutyl cyanoacrylate (PBCA), said polymer being existent in the polymerization system in the form of nanoparticles. During or after the polymerization of said monomer, a drug is added so that it is either incorporated into said nanoparticles or adsorbed onto the surface of said nanoparticles. The unexpected observation was made by Kreuter et al. that when a surfactant is added to this nanoparticle-drug complex ("coating"), drugs associated with said "surfactant-coated" nanoparticles can cross the blood-brain-barrier.

The advantage of said prior art method over previous methods (and of the prior art products obtained by said process) was that essentially any drug could be linked to the nanoparticles and delivered to the brain, without the need to alter the structure of said drug. Thus, said former Kreuter et al. invention provides the first universal method to help drugs cross the blood brain barrier.

As a specific example, drugs used to treat the nervous system in mammals, in particular in human patients, have to be able to cross the blood brain barrier (bbb). The term "blood brain barrier" (bbb) as used herein refers to the bbb in the narrower sense, i. e. in the sense this term is used usually by a person skilled in the medical field, as well as to the blood spinal barrier and blood retina barrier. Unfortunately, many drugs do not pass the bbb efficiently or not at all and are only effective when given directly into the brain. The blood brain barrier (bbb), which consists of the endothelium of the brain vessels, the basal membrane and neuroglial cells, acts to limit transport of substances into the brain. Sometimes the structure of the bbb is subdivided into two components: the endothelial or capillary barrier and the ependymal barrier Banks, W. A., Kastin, A. J., Barrera, Delivering peptides to the central nervous system: Dilemmas and strategies, Pharm. Res. 8 (1991), 1345–1350). The nature of the substance penetration through the bbb has not yet been determined but it is known that many of the regulators of brain function such as cytokines, transfernin, enkephalines, endorphines can pass through the bbb from the vessels into the brain (Raeissi & Audus 1989, Zlokovich et al. 1989, 1990). However, many substances which can affect the central nervous system (CNS) such as adenosin, β-endorphins, synthetic analogues of endogenous peptides (Houghten et al. 1980, Levin et al 1987, Sakane et al. 1989) as well as some excitatory and inhibitor amino acids and trophic factors, penetrate poorly or not at all through the bbb. At present, drugs with no bbb penetration or poor bbb penetration can only be given by direct CNS infusion. Thus, many potentially potent drugs are not useful clinically due to their inability to pass the bbb.

The teaching of Kreuter (Kreuter et al., loc. cit.) has provided a novel way of delivering drugs across the bbb. However, the fabrication of suitable nanoparticles from the selected polymers required a step wherein the nanoparticle/drug complex is coated with an appropriate surfactant such as Tween 80 (polysorbate 80). As the Kreuter et al. reference (loc. cit.) teaches, only by coating the nanoparticles with the appropriate surfactant the desired effect of passing the bbb by the drug was achieved.

While this was an important innovative step to achieve drug targeting to the brain, there is a continuous need to simplify the fabrication process and to reduce the probability of potentially toxic effects of said surfactants. It is therefore desirable to have a method available whereby nanoparticles are fabricated without the need to apply a coating to the nanoparticle drug complex. Similarly, nanoparticles having no such surfactant coating were desired. Based on these considerations, a critical and long-felt need is apparent from the prior art for a method of fabrication of a composition of nanoparticles in a manner that does not require a step of coating the nanoparticle/drug complex with surfactant(s).

A simplified and potentially less toxic method of nanoparticle fabrication is therefore needed that allows to target drugs to a specific site within or on the mammalian body. There is a need, too, for a method for targeting drugs which do not pass the bbb ("non-penetrating drugs") to penetrate the bbb. In a similar scope, it is also desirable to improve the rate of penetration of drugs that normally do pass the bbb ("penetrating drugs"). An increase of the relative amount of a drug in the brain may allow a total dose reduction, thus reducing the peripheral side effects while, at the same time, maintaining the desired biological activity in the nervous system.

SUMMARY OF THE INVENTION

To overcome the disadvantages of the prior art, the subject of the present invention is a method of preparation of non-coated nanoparticles as a drug carrier for a wide range of drugs in order to allow a targeting of the drug to a specific target in the mammalian body, specifically in order to enhance the penetration of drugs or diagnostic agents across the bbb, said method not requiring a coating procedure during fabrication of the nanoparticles. Subjects of the present invention are also the drug targeting system obtained by such a method of fabrication, the use of said drug targeting system as well as a medical treatment method by which the drug targeting system of the invention is delivered to a mammal, particularly to a human.

Accordingly, it was an object of this invention to provide a drug targeting system which allows a directed targeting of drugs to a target within the mammalian body, whereby said target could be any organ or site within (or on the surface of) the mammalian (e. g. human) body, for example the bbb or the brain. It was a further object of this invention to provide a drug targeting system which can be prepared by a method which is more simple than methods of manufacturing drug targeting systems known from the prior art (e. g. Kreuter et al.; loc. cit.). It was another object of the present invention to provide a drug targeting system which can be delivered to a mammal more conveniently, e. g. by a simple administration step and can be directed to the desired target in a high rate and with a high ratio of transfer of the drug from the site of administration to the site of pharmacological effect.

It was another object of the invention to provide a simple method of manufacture of a new drug targeting system. Specifically, it was an object to provide a simple method of manufacture which can be carried out with the same equipment used up to now, but with fewer steps of the manufacturing method. In particular, the step of coating a nanoparticle drug complex by a surfactant should be omitted as one of the objects of the present invention.

It was another object of the invention to develop a method for targeting physiologically effective substances to a specific target within or on the mammalian body. Another object of the invention was to develop a method for targeting drugs affecting the nervous system to produce a physiologic or pharmacologic effect or to apply substances with diagnostic value, which method overcomes the aforesaid disadvantages associated with the prior art.

Still another object of the present invention was to provide a method and composition for allowing non-penetrating and poorly penetrating drugs to pass the bbb more easily.

Yet another object of the invention was to provide a reliable and easily usable method and composition for treating disorders of the nervous system by systemic injection or oral application of drug-absorbed nanoparticles that do not contain a coating as disclosed in the prior art (Kreuter et al., U.S. patent application Ser. No. 08/203,326).

These and other objects and features of the invention will be apparent from the detailed description of the invention and the accompanying drawings.

The present invention relates to a drug targeting system for administration to a mammal comprising nanoparticles made of a polymeric material, said nanoparticles comprising said polymeric material, one or more physiologically effective substance(s) to be delivered to said mammal and one or more stabilizer(s) for said nanoparticles allowing targeting of said physiologically effective substance(s) to a specific site within or on a mammalian body; and a physiologically acceptable carrier and/or dilutent allowing the transport of said nanoparticles to the target within said mammal after administration.

The present invention also relates to a method for preparing a drug targeting system for administering one or more physiologically effective substance(s) to a mammal, said method comprising the steps of preparing nanoparticles made of a polymeric material, said nanoparticles comprising said polymeric material, one or more physiologically effective substance(s) to be delivered to said mammal and one or more stabilizer(s) for said nanoparticles allowing targeting of said physiologically effective substance(s) to a specific site within or on a mammalian body, by polymerizing, in a per se known manner, one or more monomeric and/or oligomeric precursor(s) of said polymeric material in the presence of said physiologically effective substance(s) and in the presence of said stabilizer(s); and optionally providing said nanoparticles in a medium allowing the transport of said nanoparticles to a target within or on said mammal after administration.

The invention furthermore relates to a method for preparing a drug targeting system for administering one or more physiologically effective substance(s) to a mammal, said method comprising the steps of preparing nanoparticles made of a polymeric material, said nanoparticles comprising said polymeric material and one or more stabilizer(s) for said nanoparticles, by polymerizing, in a per se known manner, one or more monomeric and/or oligomeric precursor(s) of said polymeric material in the presence of said stabilizer(s);

loading one or more physiologically effective substance(s) to be delivered to said mammal into and/or onto said nanoparticles; and optionally providing said loaded nanoparticles in a medium allowing the transport of said nanoparticles to the target within or on said mammal after administration.

In addition, the invention relates to the drug targeting system as defined above for medical use.

The invention relates also to the use of the drug targeting system according to the above definition and definition in the claims in the preparation of a medicament allowing one or more physiologically effective substance(s) to be targeted to a specific site within or on a mammalian body, particularly to de delivered across the blood brain barrier, more specifically across the blood brain barrier to the central nervous system.

In addition, the invention relates to a method of targeting one or more physiologically effective substance(s) to a specific target within or on a mammalian body, wherein a drug targeting system according to the above definition is administered to a mammal.

More particularly, the present invention features a method of delivering pharmacologically active substances across the blood-brain barrier and a drug targeting system useful for delivering drugs across the bbb. This invention is based on the surprising finding that treatment of nanoparticles having a drug adsorbed thereon and/or incorporated therein without coating a surfactant thereon allows the adsorbed or incorporated drug to traverse the bbb. While it is theorized that the nanoparticles cross the bbb and that the drug desorbs after transit of the nanoparticles, this step is not a necessary part of the invention so long as the drug traverses the bbb to yield its pharmacological action. The term "pharmacologically active" as used herein, means and includes not only drug pharmaceutical activity but also diagnostic activity.

The basic drug targeting system is made by a process, comprising:

formation of a suspension of nanoparticles by polymerization or dispersion using appropriate stabilizers.

sorption/incorporation of an physiologically effective substance onto and/or into the nanoparticle.

More particularly, the method of the invention comprises the steps of loading a pharmacologically active substance such as a drug onto or into a nanoparticle, administering the nanoparticles (which are not surrounded by a coating) to a mammal in a manner which allows the pharmacologically active substance to reach and cross the bbb, and allowing the pharmacologically active substance to be released from the nanoparticle to achieve the desired pharmacological effect. It is not clear whether the nanoparticles themselves cross the bbb or only the pharmacologically active substance crosses the bbb by being released from the nanoparticle. However, the exact mechanism is not decisive as long as the pharmacological effect is achieved.

The nanoparticles are loaded with the drug by any known loading step. Commonly, solid nanoparticles are used and are loaded by sorption of the drug onto the surface of the nanoparticle, e. g. by soaking the preformed nanoparticle in a solution of the drug. However, in some circumstances, the drug is added to the polymerization solution and the drug is incorporated into the nanoparticle as the nanoparticle is made. In the prior art, dextran has been used as a stabilizer and polysorbate 80 as a surfactant (Kreuter et al.; loc. cit.).

The critical, innovative step in the present invention is that during the polymerization of the polymeric material to form the nanoparticles, stabilizers other than Dextran 70.000 are used. For example, polysorbates or, alternatively, Dextran having a molecular weight smaller than 70.000 may be used to achieve the desired effect of delivering a drug across the bbb. In a preferred embodiment of the present invention, Dextran 12.000 or polysorbate 85 (Tween 85) is used. These stabilizers are cited for purposes of illustration only, and the selection of any other stabilizer(s) or their combination with the above two stabilizers which may be used to achieve the desired effect is intended not to be limited. Thus, as long as the nanoparticles are fabricated with an appropriate stabilizer, they are useful as a drug targeting system. There is no need to apply an additional coating which surrounds the nanoparticle drug complex as taught by Kreuter et al. (Kreuter et al.; loc. cit.). The method of the present invention considerably simplifies the fabrication procedure and facilitates clinical application as mixing with a surfactant is no longer required prior to application to the organism.

Simply mixing of preformed nanoparticles and the drug for adsorption is sufficient to prepare a drug targeting system which enables the passage of the drug across the bbb. A major advantage of the composition obtained by the above method is that the drug targeting system can be used to transport drugs across the bbb. In other words: Drugs which otherwise could not cross the bbb to reach the central nervous system or could not pass across the bbb in sufficient amounts to exert a desired phlarmacological or diagnostic activity can reach the desired target when transported by the drug targeting system of the invention.

Other objects, features, and advantages of the invention will be apparent to those skilled in the art from the detailed description of the invention which will now follow, taken in conjunction with the tables, drawings, and the accompanying claims.

BRIEF DESCRIPTION OF THE DRAWINGS

The drawings are not drawn to scale. They are set forth to illustrate various embodiments of the inventions and the results achieved. The drawings, to which reference will be made, are as follows:

FIG. 1A displays a monolithic nanoparticle (N) with a drug dispersed or dissolved in a matrix (D). FIG. 1B displays a capsule-type nanoparticle with drug entrapped in the interior. FIG. 1C displays a nanoparticle with a drug absorbed or absorbed on the surface of the nanoparticle. These three embodiments are not limiting because combinations thereof are possible.

Group 1: dalargin solution in PBS (10 mg/kg);

Group 2: suspension of empty nanoparticles (40 mg/kg) stabilized with polysorbate 85;

Group 3: polysorbate 85 in PBS (1%);

Group 4: dalargin loaded by incubating for 3 h onto empty nanoparticles (10 mg/kg) which were stabilized with polysorbate 85.

DESCRIPTION OF THE PREFERRED EMBODIMENTS

It should be understood that the detailed description and specific examples, while indicating preferred embodiments of the invention, are given by way of illustration only, since various changes and modifications within the spirit and the scope of the invention will become apparent to those skilled in the art from this description and the accompanying drawings as well as from the claims.

The term "nanoparticles" as used herein denotes a carrier structure which is biocompatible and sufficiently resistant to chemical and/or physical destruction by the environment of use such that a sufficient amount of the nanoparticles remain substantially intact after entry into the mammalian body following intraperitoneal or oral administration so as to be able to reach the desired target, e. g. the brain and/or the bbb. Usually, nanoparticles are solid colloidal particles. Drugs or other relevant materials (e. g. those used for diagnostic purposes in nuclear medicine or in radiation therapy) can be dissolved within the nanoparticles, entrapped, encapsulated and/or adsorped or attached.

The nanoparticles are synthetic particles made of a natural or synthetic polymeric material. The particles have a diameter of below 1,000 nm, preferably between about 1 to 1,000 nm.

In the drug targeting system of the invention, the nanoparticles preferably comprise a polymeric material which selected from the group consisting of polyacrylates, polymethacry-lates, polybutylcyanoacrylates, polyarylamides, polylactates, polyglycolates, polyanhydrates, polyorthoesters, gelatin, polysaccharides, albumin, polystyrenes, polyvinyls, polyacrolein, polyglutaraldehydes and derivatives, copolymers and mixtures thereof. Monomer materials particularly suitable to fabricate biodegradable nanoparticles by emulsion polymerization in a continuous aqueous phase include methylmethacrylates, alkylcyanoacrylates, hydroxyethyl-methacrylates, methacrylic acid, ethylene glycol dimethacrylate, acrylamide, N,N'-bismethylene acrylamide and 2-dimethylaminoethyl methacrylate. Other nanoparticles are made by different techniques from N,N-L-lysinediylterephthalate, alkylcyanoacrylate, polylactic acid, polylactic acid-polyglycolic acid-copolymers, polyanhydrates, polyorthoesters, gelatin, albumin, and desolvated macromolecules or carbohydrates. Further, also non-biodegradable materials can be used such as polystyrene, poly(vinylpyridine), polyacroleine and polyglutaraldehyde. A summary of materials and fabrication methods has been published (see J. Kreuter, (1991) Nanoparticles-preparation and applications. In: M. Donbrow (Ed.) *Microcapsules and nanoparticles in medicine and pharmacy.* CRC Press, Boca Ranton, Fla., pp. 125–14). The polymeric materials which are formed from monomeric and/or oligomeric precursors in the polymerization/nanoparticle generation step, are per se known from the prior art, as also the molecular weights and molecular weight distribution of the polymeric material which a person skilled in the field of manufacturing nanoparticles may suitably select in accordance with the usual skill. Reference is, in this respect, made to Kreuter et al., loc. cit., and the references cited therein.

The nanoparticles of the drug targeting system of the present invention may either comprise a physiologically effective substance or may comprise more than one, e. g. two or more, physiologically effective substances to be delivered to a target within or on the mammalian body in the form adsorbed thereto, absorbed therein or incorporated therein. The term "adsorbed thereto", as used in the present specification and claims, means that the physiologically effective substance(s) is/are adsorbed to the outer surface of the nanoparticles by adsorptive forces. The terms "absorbed therein" and "incorporated therein", as used in the present specification and claims, mean in a similar manner that the physiologically effective substance or substances is/are contained in the inner volume of the nanoparticles. The substance(s) may have been absorbed or incorporated into the nanoparticle on any suitable way which is at present not considered decisive for the results of the present invention. Suitable ways may be the incorporation of the physiologically effective substance during the polymerization process before or during the step of forming the nanoparticle shell or the absorption after final formation of the nanoparticle shell by transfer through the nanoparticle shell or even both ways.

The term "physiologically effective substance" as used in the present specification and claims is defined here in the broadest sense, i. e. including any natural or synthetic substance which may have a physiological effect when administered to a mammal. The physiologically effective substance (such as a drug) that can be suitably employed in accordance with the invention with warm blooded animals, particularly mammals including humans, veterinarian animals and farm animals, are all those affecting, acting on, or being visualized at a desired target within or on the mammalian body, for example within the nervous system, including tumor tissue located therein.

The terms "pharmacologically active substance" or "drug" are sometimes used in the present specification, too, and are intended to have a similar meaning which is intended not to restrict the term "physiologically effective substance" as used herein. In preferred embodiments of the invention, the physiologically effective substance to be delivered to said mammal comprises therapeutic agents and diagnostic agents. It is possible in accordance with the invention that the drug targeting system comprises one drug or comprises more than one drugs, e. g. two or even more drugs, as long as the drugs are compatible with each other in the same nanoparticle and/or drug targeting system and exhibit physiological effects which are not directed against each other (e. g. agonist drug and antagonist drug). In more preferred embodiments and if more than one drug is present, the drugs exert a synergistic effect.

In even more preferred embodiments of the drug targeting system of the invention, the physiologically effective substance(s) comprise(s) a substance which has central nervous activity but cannot cross the blood brain barrier without modification and/or without a carrier. Particularly, but not exclusively, the present invention may be applied to deliver any agent for the treatment of disorders affecting the nervous system.

Specific examples of physiologically effective substances or drugs which—of course—do not restrict the present invention are therapeutic agents selected from the group consisting of drugs acting at synaptic sites and neuroeffector junctional sites; general and local analgetics; hypnotics and sedatives; drugs for the treatment of psychiatric disorders such as depression and schizophrenia; anti-epileptics and anticonvulsants; drugs for the treatment of Parkinson's and Huntington's disease, aging and Alzheimer's disease; excitatory amino acid antagonists, neurotrophic factors and neuroregenerative agents; trophic factors; drugs aimed at the treatment of CNS trauma or stroke; drugs for the treatment of addiction and drug abuse; antacoids and anti-inflammatory drugs; chemotherapeutic agents for parasitic infections and diseases caused by microbes; immunosuppressive agents and anti-cancer drugs; hormones and hormone antagonists; heavy metals and heavy metal antagonists; antagonists for non-metallic toxic agents; cytostatic agents for the treatment of cancer; diagnostic substances for use in nuclear medicine; immunoactive and immunoreactive agents; transmitters and their respective receptor agonists and receptor antagonists, their respective precursors and metabolites; transporter inhibitors; antibiotics; antispasmodics; antihistamines; antinauseants; relaxants; stimulants; sense and antisense oligonucleotides; cerebral dilators; psychotropics; antimanics; vascular dilators and constrictors; anti-hypertensives; drugs for migraine treatment; hypnotics, hyperglycemic and hypoglycemic agents; minerals and nutritional agents; anti-obesity drugs; anabolics; antiasthmatics; and mixtures thereof.

These substances are decribed by Gilman et al. (1990) "Goodman and Gilman's—The Pharmacological Basis of Therapeutics", Pergamon Press, New York, and include the following agents:

acetylcholine and synthetic choline esters, naturally occuring cholinomimetic alkaloids and their synthetic congeners, anticholinesterase agents, ganglionic stimulants, atropine, scopolamine and related antimuscarinic drugs, catecholamines and sympathomimetic drugs, such as epinephrine, norepinephrine and dopamine, adrenergic agonists, adrenergic receptor antagonists, transmitters such as GABA, glycine, glutamate, acetylcholine, dopamine, 5-hydroxytryptamine, and histamine, neuroactive peptides;

analgesics and anesthaetics such as opioid analgesics and antagonists; preanesthetic and anesthetic medications such as benzodiazepines, barbiturates, antihistamines, phenothiazine and butylphenones; antiemetics; anticholinergic drugs such as atropine, scopolamine or glycopyrrolate; cocaine; chloral derivatives; ethchlorvynol; glutethimide; methyprylon; meprobamate; paraldehyde; disulfiram; morphine, fentanyl and naloxone;

centrally active antitussive agents;

psychiatric drugs such as phenothiazines, thioxanthenes and other heterocyclic compounds (e.g. halperiodol); tricyclic antidepressants such as desimipramine and imipramine; atypical antidepressants (e.g. fluoxetine and trazodone), monoamine oxidase inhibitors such as isocarboxazid; lithium salts; anxiolytics such as chiordiazepoxyd and diazapam;

anti-epileptics including hydantoins, anticonvulsant barbiturates, iminostilbines (such as carbamazepine), succinimides, valproic acid, oxazolidinediones and benzodiazepines;

anti-Parkinson drugs such as L-DOPA/carbidopa, apomorphine, amantadine, ergolines, selegeline, ropinorole, bromocriptine mesylate and anticholinergic agents;

antispasticity agents such as baclofen, diazepam and dantrolene;

neuroprotective agents, such as excitatory amino acid antagonists, for example NMDA or AMPA-antagoniststs, neurotrophic factors and brain derived neurotrophic factor, ciliary neurotrophic factor, or nerve growth factor; neurotrophine 3 (NT3); NT4 and NT5; gangliosides; neuroregenerative agents;

drugs for the treatment of addiction and drug abuse including opioid antagonists and anti-depressants;

antacoids and anti-inflammatory drugs such as histamine, bradykinin, kallidin and their respective agonists and antagonists;

immunosuppressive agents such as FK506, chemotherapeutic agents for parasidic infections and microbial diseases;

anti-cancer drugs including alkylating agents (e.g. nitrosoureas) and antimetabolites; nitrogene mustards, ethylenimines and methylmelamines; alkylsulfonates; folic acid analogs; pyrimidine analogs, purine analogs, vinca alcaloids; antibiotics;

anti-inflammatory drugs such as phenylbutazone, indomethacin, naproxen, ibuprofen, flurbiprofen, diclofenac, dexamethasone, prednisone and prednisolone;

cerebral vasodilators such as soloctidilum, vincamine, naftidrofuryl oxalate, codergocrine mesylate, cyclandelate, papaverine, nicotinic acid, anti-infective agents such as erythromycin stearate, and cephalexin.

As explained above, the term "drugs" may also include diagnostic agents. In the broadest sense, diagnostic agents suitable for inclusion into the drug targeting system of the invention are agents which are used in recognizing or differentiating diseases in a mammalian body. In preferred embodiments, the drug targeting system of the invention comprises diagnostic agents useful in the diagnosis in nuclear medicine and in radiation therapy.

A critical component of nanoparticles of the drug targeting system according to the invention is/are the stabilizers. In preferred embodiments, only one stabilizer is used. In this case, the targeting of the physiologically effective substance(s) or drug(s) to a specific site within or on the mammalian body can be achieved in an ideal manner. For example, a drug can be brought to and allowed to pass the blood brain barrier (bbb) in a very effective manner so that the amount of effective substance at the site of effect is considerably enhanced, and the dose administered to the mammal can be reduced correspondingly. However, it is also possible to use more than one, e. g. two or more, stabilizer(s).

Basically, each stabilizer allowing to achieve the object of the present invention is suitable to be incorporated into the drug targeting system of the invention. However, it was found that, in distinguishing the present invention from the prior art Kreuter at al., loc. cit., a stabilizer other than dextran 70.000 should be used.

In preferred embodiments of the invention, said stabilizer for said nanoparticles being part of the drug targeting system of the invention is selected from the group consisting of stabilizers which allow a passage of said nanoparticles including said physiologically effective substance(s) through the blood brain barrier in said mammal and stabilizers which allow a release of said physiologically effective substance(s) from said nanoparticles and a passage of said physiologically effective substance(s) through the blood brain barrier separate from said nanoparticles.

In an even more preferred embodiment, said stabilizer is one allowing a passage of said physiologically effective substance(s) through the blood brain barrier without chemical modification of said physiologically effective substance (s).

Specifically advantageous drug targeting systems according to the invention contain nanoparticles, wherein said stabilizer comprises a substance selected from the group consisting of polysorbate 85, dextran 12.000, carboxylic acid esters of multifunctional alcohols, polysorbates, poloxameres, poloxamines, alkoxylated ethers, alkoxylated esters, alkoxylated mono-, di and triglycerides, alkoxylated phenols and diphenols, substances of the Genapol® and Bauki® series, metal salts of carboxylic acids, metal salts of alcohol sulfates and metal salts of sulfosuccinates and mixtures of two or more of said substances, wherein said Genapol® compounds are of the formulas wherein y is in the range of 4 to 18 and x is in the range of 1 to 18, and said Bauki® compounds are of the formulas (I) or (I')

in which $R_1$, $R_2$, $R_5$ and $R_6$ are identical and represent hydrogen and a methyl or ethyl group, Q represents a valency, oxygen or an ester or amide bridge and Q' denotes dydrogen if Q represents a valency or oxygen, and is a hydroxyl or amino group if Q represents an ester or amide bridge, x is an integer from 3 to 50, if Q is a valency or oxygen, and an integer from 3 to 1000 if Q is an ester or amide function, $G_1$ and $G_2$ are a valency, oxygen or an ester or amide group, it being possible for the two groups to be identical or different, n is an integer from 4 to 44, y is an integer from 2 to 50, and $R_3$ is hydrogen or a lower alkyl having 1–6 C atoms.

For example, said stabilizer comprises a substance selected from the group consisting of polysorbate 85, polysorbate 81, dextran 12.000, carboxylic acid esters and preferably fatty acid esters of glycerol and sorbitol, even more preferably glycerol monostearate, sorbitan monostearate and sorbitan monooleate, poloxamer 188 (Pluronic® F68), ethoxylated ethers, ethoxylated esters, ethoxylated triglycerides, ethoxylated phenols and diphenols, metal salts of fatty acids and metal salts of fatty alcohol sulfates, preferably sodium salts of fatty acids and of fatty alcohol sulfates, even more preferably sodium stearate and sodium lauryl sulfate and mixtures of two or more of said substances.

In the practice of the invention, it has turned out that drug targeting systems yield especially good results, wherein said stabilizer of the nanoparticles comprises a substance selected from the group consisting of polysorbate 85 or dextran 12.000 and mixtures thereof and mixtures of said stabilizers with other stabilizers as mentioned above. When using such drug targeting systems, the step of targeting the physiologically effective substance(s) to a specific site within or on the mammalian body could be very well accomplished. In particular, in the step of targeting drugs to the blood brain barrier and penetrating said drugs across said bbb, a relatively high effective amount of said drug in the brain available for action in the central nervous system was found. Thus, the efficiency of passage of said drug across the bbb could be enhanced, while the amount of drug targeting system in the form of drug-loaded nanoparticles could particularly be reduced if the nanoparticles contained polysorbate 85 and/or dextran 12.000 as the stabilizers, optionally in admixture with other stabilizers.

As a further component, the drug targeting system of the invention comprises a physiologically acceptable carrier and/or diluent allowing the transport of said nanoparticles to the target within said mammal after administration. Preferably, said carrier and/or diluent is/are selected from the group consisting of water, physiologically acceptable aqueous solutions containing salts and/or buffers and any other solution acceptable for administration to a mammal. Such carriers and diluents are well known to a person skilled in this field and comprise distilled water, de-ionized water, pure or ultrapure water, saline, phosphate-buffered saline (PBS), solutions containing usual buffers which are compatible with the other components of the drug targeting system etc..

In general, nanoparticles can be produced by conventional methods, including emulsion polymerization in a continuous aqueous phase, emulsion polymerization in continuous organic phase, interfacial polymerization, solvent deposition, solvent evaporation, dissolation of an organic polymer solution, cross-linking of water-soluble polymers in emulsion, dissolution of macromolecules and carbohydrate cross-linking. These fabrication methods can be performed with a wide range of polymer materials mentioned above.

Typical materials suitable for stabilizing the nanoparticles are selected from the group of substances mentioned above. The choice of the monomer and/or polymer, the solvent, the emulsifier, the stabilizer and other auxilliary substances will be dictated by the particular nanoparticle being fabricated and can be chosen, without limitation and difficulty, by those skilled in the art.

The ratio of the drug to polymer can vary within a wide range. Preferably, it is the range of 1:100 to 1:1. Also, the removal of the solvent or emulsifier can be achieved in a number of different ways, which are known and, hence, need not to be repeated here.

In a preferred embodiment of the present process, during the polymerization step (i. e. when the nanoparticles are formed) a polymeric material is made which is selected from the group consisting of polyacrylates, polymethacrylates, polybutylcyanoacrylates, polyarylamides, polylactates, polyglycolates, polyanhydrates, polyorthoesters, gelatin, polysaccharides, albumin, polystyrenes, polyvinyls, polyacrolein, polyglutaraldehydes and derivatives, copolymers and mixtures thereof.

Even more advantageous and, hence, preferred is a process for manufacturing nanoparticles wherein said loading step comprises mixing said nanoparticles with a solution of said physiologically effective substance(s) and allowing a sufficient time for an effective amount of said physiologically effective substance(s) to be adsorbed onto and/or absorbed by said nanoparticles.

As already pointed our above, the step of selecting the suitable stabilizer for the nanoparticle is decisive. Hence, a skilled person will carefully select the stabilizer which, according to the present invention and in contrast to Kreuter et al. (loc. cit.) is a stabilizer other than dextran 70.000. Preferably, there is/are used as the stabilizer(s) for said nanoparticles one or more substances selected from the group consisting of stabilizers which allow a passage of said nanoparticles including said physiologically effective substance(s) through the blood brain barrier in said mammal and stabilizers which allow a release of said physiologically effective substance(s) from said nanoparticles and a passage of said physiologically effective substance(s) through the blood brain barrier separate from said nanoparticles.

A similarly preferred embodiment of the invention is a process, wherein as said stabilizer(s), there is/are used one or more substances allowing a passage of said physiologically effective substance(s) through the blood brain barrier without chemical modification of said physiologically effective substance(s).

Exemplary for the invention is a method, wherein as said stabilizer(s), there is/are used one or more substance(s) selected from the group consisting of polysorbate 85, dextran 12.000, carboxylic acid esters of multifunctional alcohols, polysorbates, poloxameres, poloxamines, alkoxylated ethers, alkoxylated esters, alkoxylated mono-, di and triglycerides, alkoxylated phenoles and diphenoles, substances of the Genapol® and Bauki® series, metal salts of carboxylic acids, metal salts of alcohol sulfates and metal salts of sulfosuccinates and mixtures of two or more of said substances.

Particularly preferred is a method, wherein as said stabilizer(s), there is/are used one or more substance(s) selected from the group consisting of polysorbate 85, polysorbate 81, dextran 12.000, carboxylic acid esters and preferably fatty acid esters of glycerol and sorbitol, even more preferably glycerol monostearate, sorbitan monostearate and sorbitan monooleate, poloxamer 188 (Pluronic® F68), ethoxylated ethers, ethoxylated esters, ethoxylated triglycerides, ethoxylated phenoles and diphenoles, metal salts of fatty acids and metal salts of fatty alcohol sulfates, preferably sodium salts of fatty acids and of fatty alcohol sulfates, even more preferably sodium stearate and sodium lauryl sulfate and mixtures of two or more of said substances.

If as said stabilizer(s), there is/are used one or more substance(s) selected from the group consisting of polysorbate 85 and dextran 12.000 and mixtures thereof and mixtures of said stabilizers with other stabilizers, particularly good results in respect of a simple process and highly suitable nanoparticles are obtained.

It could be shown that, in the course of the present process, a great number of therapeutic agents and/or diagnostic agents can be incorporated into or adsorbed onto nanoparticles. Hence, a method is particularly preferred, wherein as said physiologically effective substance(s), there is/are used one or more substance(s) selected from the group consisting of a therapeutic agent and a diagnostic agent. Specifically preferred is a method, wherein as said physiologically effective substance(s) there is/are used a substance/substances which has/have central nervous system activity but cannot cross the blood brain barrier without modification or without a carrier.

At present, there are methods for manufacturing a drug targeting system which are preferred in view of the good results which are achieved. In these methods, there is/are used as the therapeutic agent a substance/substances which is/are selected from the group consisting of drugs acting at synaptic sites and neuroeffector junctional sites; general and local analgetics; hypnotics and sedatives; drugs for the treatment of psychiatric disorders such as depression and schizophrenia; anti-epileptics and anticonvulsants; drugs for the treatment of Parkinson's and Huntington's disease, aging and Alzheimer's disease; excitatory amino acid antagonists, neurotrophic factors and neuroregenerative agents; trophic factors; drugs aimed at the treatment of CNS trauma or stroke; drugs for the treatment of addiction and drug abuse; antacoids and anti-inflammatory drugs; chemotherapeutic agents for parasitic infections and diseases caused by microbes; immunosuppressive agents and anti-cancer drugs; hormones and hormone antagonists; heavy metals and heavy metal antagonists; antagonists for non-metallic toxic agents; cytostatic agents for the treatment of cancer; diagnostic substances for use in nuclear medicine; immunoactive and immunoreactive agents; transmitters and their respective receptor agonists and receptor antagonists, their respective precursors and metabolites; transporter inhibitors; antibiotics; antispasmodics; antihistamines; antinauseants; relaxants; stimulants; sense and antisense oligonucleotides; cerebral dilators; psychotropics; antimanics; vascular dilators and constrictors; anti-hypertensives; drugs for migraine treatment; hypnotics, hyperglycemic and hypoglycemic agents; minerals and nutritional agents; anti-obesity drugs; anti-asthmatics; and mixtures thereof. However, these therapautic substances are to be considered as examples only and are not limiting the invention.

In a similar manner, non-limiting examples of methods employing a diagnostically useful agent are methods wherein as said diagnostic agent, there is/are used a substance/substances selected from the group consisting of diagnostics useful in the diagnosis in nuclear medicine and in radiation therapy.

In the method of the invention for manufacturing the drug targeting system, it is usual, but not necessary to provide the nanoparticles loaded with the physiologically effective substance(s) and stabilized with a suitable stabilizer in a medium allowing the transport of said nanoparticles to a target within or on a mammalian body after the administration of said nanoparticles to the mammal. The medium can generally be every medium by which the desired purpose is achieved and which does not affect the nanoparticles' capability to be directed to the desired target and to transport the physiologically effective agent to this target for the desired pharmacological effect. Particularly, the medium should not deteriorate the pharmacological potency of the therapeutic or diagnostic agent and the capability of the stabilizer to direct the nanoparticles to a desired target within or on the mammalian body. It has been turned out that, in preferred embodiments of the method to manufacture the drug targeting system, said medium allowing the transport of said nanoparticles to the target within said mammal after administration is selected from the group consisting of water, physiologically acceptable aqueous solutions containing salts and/or buffers and any other solution acceptable for administration to a mammal.

In accordance with the present invention nanoparticles are able to carry (or deliver) drugs or diagnostics to a specific desired target, for example to the bbb, and decisively contribute to penetrate therapautically and/or diagnostically useftil substances across the bbb. At the present time, it is not possible by traditional concepts to show the concrete mechanism of the penetration of said substances across the bbb, although speculations can be made. However, it is not intended to be bound by any theory.

Banks et al. (1991) suggested some mechanisms of peptide transport to the brain which may also apply to nanoparticles or materials carried by nanoparticles. Transport can be achieved by non-saturable and saturable means, as intact molecules or their metabolites. The degree of bbb passage depends primarily on lipid solubility of the molecule (Banks, W. A., Kastin, A. J., Peptides and blood-brain-barrier: Lipophilicity as a predictor of permeability" Brain Res. Bull. 15, 287–292, 1985). Other factors that may influence brain entry are molecular weight, charge, degree of protein binding in the serum, although these seem to play a less important role than lipophilicity (Banks et al. 1991). The transport mechanism suggested by Banks seem to be restricted to transporting a limited number of structurally related peptides such as met-enkephalin and a few other closely related peptides. They do not apply, for instance, to b-endorphines and kyotorphines. Saturable transport rates are modulated by various factors, including some substances, like leucine and aluminum (Banks and Kastin 1990). Whether transport mechanisms of nanoparticles are similar to transport of peptides is currently not known. As the present invention is the first do demonstrate transport of nanoparticle without coating to the CNS with physiologically effective substances, no further information is available at present.

The drug targeting system explained above is a novel system. As already addressed above, it can be advantageously used in the medical field. A particular field of use is the use targeting physiologically effective substances to a target within or on the mammalian body.

Preferably, the novel drug targeting system is used in the preparation of a medicament allowing one or more physiologically effective substance(s) to be targeted to a specific site within or on a mammalian body.

In the course of research resulting into the present invention, it was found that one specific field of use of the present drug targeting system is the use in the preparation of a medicament allowing one or more physiologically effective substance(s) to be delivered across the blood brain barrier of a mammal. If the drug targeting system is used in this manner, this may contribute to achieving a pharmacological effect in the central nervous system of a mammal which could up to now not be achieved in such an efficient manner. In particularly preferred embodiments of the invention, the use of the present drug targeting system was possible in the preparation of a medicament achieving a pharmacological effect in the central nervous system of a mammal by the action of one or more physiologically effective substance(s) otherwise not passing the blood brain barrier. Similarly preferred is the use of the present drug targeting system in the preparation of a medicament achieving a pharmacological effect in the central nervous system of a mammal by the action of one or more physiologically effective substance(s) otherwise passing the blood brain barrier in an amount being not or not sufficiently pharmacologically effective.

When the drug targeting system is used in the manner outlined above, this will result in the preparation of a medicament which is adapted for an oral, intravenous, subcutaneous, intramuscular, intranasal, pulmonal or rectal administration. In view of the great advantages in practical handling of the drug targeting. system, the adminsitration routes of the oral or intravenous administration are mostly preferred. The physiologically effective substance(s) can be directed efficiently to the desired target, for example can pass across the bbb easily, can thus reduce the peripheral side effects of physiologically effective substances, can considerably enhance the relative amount of such substances reaching the site of pharmacological action and, thus, contribute to reduce the amount of drug or diagnostic agent administered to the mammal. Particularly preferred is the use of the novel drug targeting system in the preparation of a medicament for administration to a human.

The present invention also concerns a method of targeting one or more physiologically effective substance(s) to a specific target within or on a mammalian body, wherein a drug targeting system according to the above definition is administered to a mammal.

The administration of said drug targeting system can be carried out generally in any desired manner or on any desired route in order to achieve that said drug targeting system is entered into the blood stream of said mammal and is transported thereby to the bbb. At present, an administration is preferably effected on an oral, intravenous, subcutaneous, intramuscular, intranasal, pulmonal or rectal route, more preferably on the oral or intravenous route. The latter routes are particularly preferred in view of the efficient way to transport said drug targeting system to the site of action within or on the mammalian body.

In the most preferred embodiment of the method of targeting one or more physiologically effective substance(s) to a specific target within or on a mammalian body, a passage of one or more physiologically effective substance(s) through the blood brain barrier is effected by administering said drug targeting system to said mammal and allowing a sufficient time to pass until a pharmacologically effective amount of said physiologically effective substance(s) has passed the blood brain barrier. In this manner, the physiologically effective substance(s) can be directed efficiently to the desired target, for example can pass across the bbb easily, can thus reduce the peripheral side effects of physiologically effective substances, can considerably enhance the relative amount of such substances reaching the site of pharmacological action and, thus, contribute to reduce the amount of drug or diagnostic agent administered to the mammal. Particularly preferred is the present method of targeting the novel drug targeting system to a specific target within or on a human by administering said drug targeting system to a human on one of the above-referenced routes of administration.

The invention is further exemplified by the following non-limiting examples.

EXAMPLE 1

In the one preferred embodiment, the nanoparticles are made from polyalkyl cyanoacrylates (hereafter also referred to as "polybutylcyanoacrylate") of the general formula:

In this example of the present invention, the nanoparticles were prepared using an acidic polymerization medium containing polysorbate 85 as stabilizer (polysorbate 85 1% in 0.01 N HCl; polysorbate 85, obtainable under the trade name "Tween® 85", is a poly-oxyethylene (20) sorbitan trioleate manufactured by Deutsche ICI GmbH, Germany, and is, in accordance with the information provided by the manufacturer a mixture of partial esters of sorbitol and its anhydrides with oleic acid, copolymerized with (on average) 20 moles ethylene oxide per molecule sorbitol). In the in vitro study, there was used butylcyano-acrylate which was added in an amount to obtain a 1% nanoparticle suspension. The mixture was agitated by stirring with a magnetic stirrer at 600 rpm for 4 h to allow nanoparticle formation. The resulting suspension was neutralized with 0.1 N sodium hydroxide solution, filtered through a sintered glass filter (pore size 16 to 40 µm), washed by centrifugation, and 4% of mannitol was added to improve redispersability of the nanoparticles after lyophilization. Particle size determination was done by means of photon correlation spectroscopy with a autoSizer Lo-C (Malvern Instruments Ltd., UK). An average diameter of 300 nm was observed. The nanoparticle suspension was then lyophilized.

EXAMPLE 2

To evaluate whether substances of the Dextran series are useful to serve the function of the stabilizer, there was also evaluated a low molecular weight member of the Dextran series (having a lower molecular weight than Dextran 70.000). Thus, another embodiment of nanoparticle fabrication used Dextran 12.000 as the stabilizer (1% in 0.01 N HCl) (Dextran 12.000 obtained from Sigma, Germany; according the information of the manufacturer, this product is a polysaccharide having an average molecular weight of 12,000 g/mole, which was produced by Leuconostoc mesenteroides strain No. B.512). In the in vitro study, butylcyanoacrylate was used as the monomer for the nanoparticle polymerization. The monomer was added to obtain a 1% nanoparticle suspension.

Again, the mixture was agitated by stirring with a magnetic stirrer at 600 rpm for 4 h to allow nanoparticle formation. The resulting suspension was neutralized with 0.1 N sodium hydroxide solution, filtered through a sintered glass filter (pore size 16 to 40 μm), washed by centrifugation, and 4% of mannitol was added to improve redispersability of the nanoparticles after lyophilization. Particle size determination was done as described above.

While these examples demonstrate a useful method to fabricate nanoparticles, they should in no way be viewed as limiting with regard to the specific fabrication parameters. The only limitation is that stabilizers other than dextran 70.000 are useful.

Figure 1:
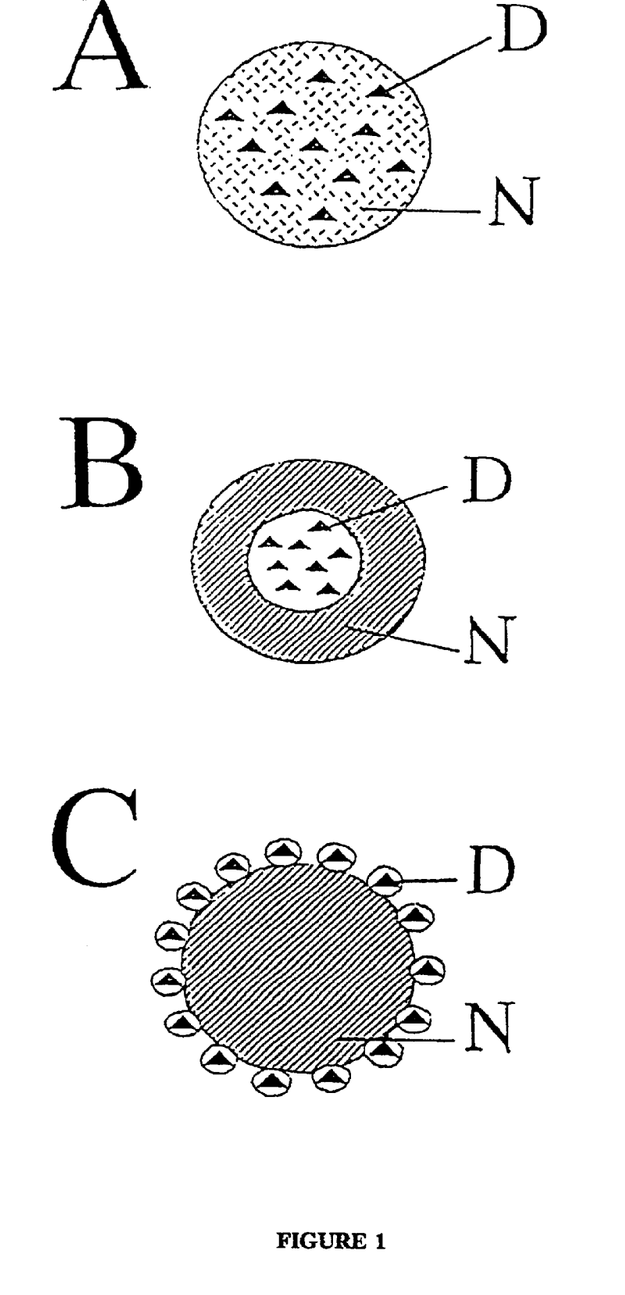
FIG. 1 is a schematic drawing of a nanoparticle, indicating its molecular structure.

FIG. 1 displays various alternatives of how nanoparticles may be fabricated and how drugs may be dispersed therein.

EXAMPLE 3

1. In order to test the pharmacological usefulness of this approach, the nanoparticles of Examples 1 and 2 were adsorbed with a drug which does not pass the bbb when given systematically, the leu-enkephalin analogue dalargin. Dalargin is a highly potent analgesic when injected directly into the brain, but it is without effect when given peripherally.

Dalargin was adsorbed to poly(butyl cyanoacrylate) nanoparticles which were stabilized with polysorbate 85. The adsorption step was carried out in PBS as the solvent for dalargin by stirring the above nanoparticles (solid nanospheres having an average particle diameter of about 300 nm) in said dalargin solution which had a content of said analgesic compound in said solvent of 1 mg/ml PBS for a time of 3 h.

After this time, the preparation was injected intravenously into mice at a dalargin dose of 10.0 mg/kg. Various preparations include pure dalargin solution and empty nanoparticles served as controls.

Figure 2:
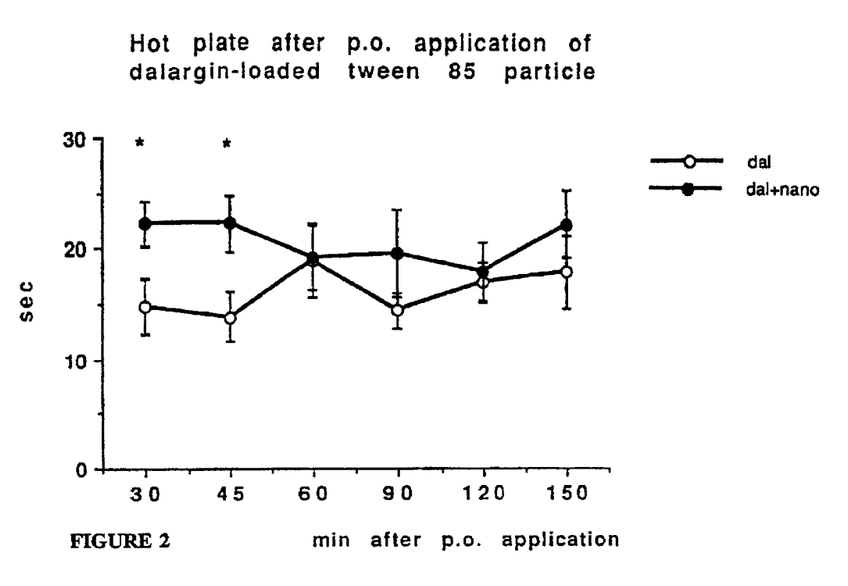
FIG. 2 illustrates the analgesic effect as demonstrated with the hot plate test after intravenous injection of dalargin (10 mg/kg). Dalargin was given either in solution, or after sorptive binding to nanoparticles. The data were collected at different time points following injection. The groups (n=10) are as follows.

Activity threshold was measured with the hot plate test. Dalargin, when dissolved in phoshate buffered saline (PBS) up to a dose of 10.0 mg/kg, did not exhibit any analgesic effect after i.v. injection (FIG. 2). In fact, only dalargin absorbed to polysorbate 85-stabilized nanoparticles had an analgesic activity which became statistically significant.

The results are displayed in FIG. 2. None of the control groups (empty nanoparticles and dalargin alone) exhibited any analgesic effects in the mice which received said comparative drug targeting system not in accordance with the present invention.

Figure 3:
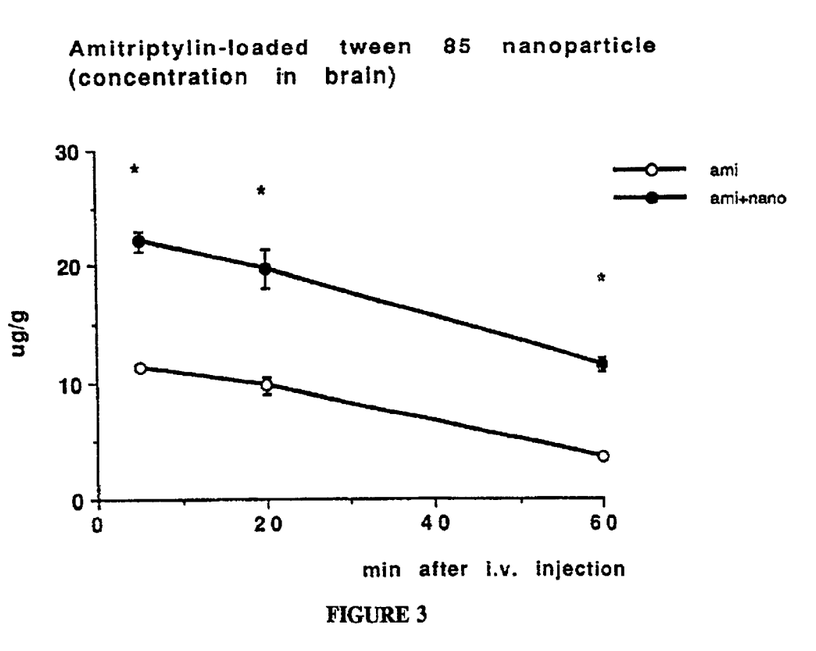
FIG. 3 illustrates the analgesic effect as demonstrated with the hot plate test after oral application of dalargin (10 mg/kg). Dalargin was given either in solution, or after sorptive binding to nanoparticles. The data were collected at different time points following oral application.

2. The per os application of dalargin-loaded polysorbate 85 nanoparticles led to increased analgesia on the hot plate test (FIG. 3). The analgesia was determined 30, 45, 60, 90, 120 and 150 min after p.o. application.

Figure 4:
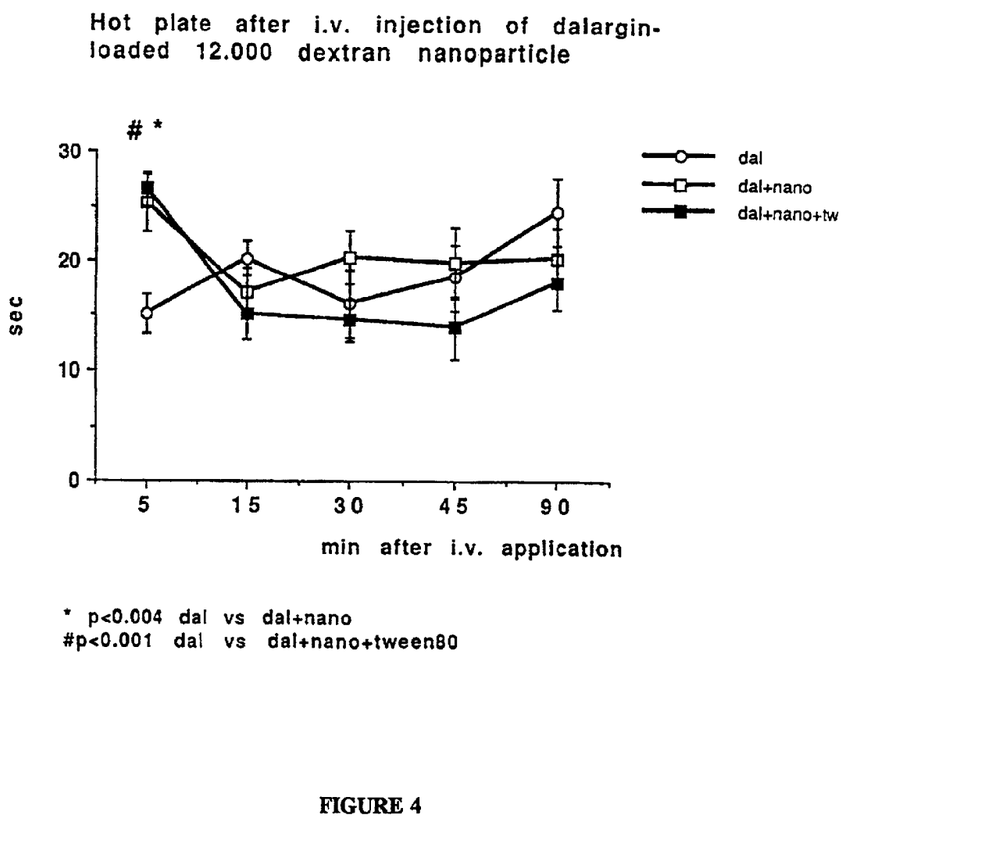
FIG. 4 illustrates brain levels of amitryptiline after i.v. injection of amitryptiline alone or when given in combination with nanoparticles. Amitryptiline was assayed using HPLC-analysis from brain homogenate.

3. In the same manner the brain level of amitriptyline was determined after injection of amitriptyline-loaded polysorbate 85 nanoparticles prepared according to Example 1. As depicted from FIG. 4, there could be shown a higher concentration of amitriptyline in brain when the drug was adsorbed onto the polysorbate 85 stabilized nanoparticles.

4. To test the question whether other stabilizers may be used to achieve the desired effect, nanoparticles were investigated in which the stabilizer was the low molecular size dextran 12,000. The dextran 12,000 stabilized nanoparticles of Example 2 were loaded with dalargin, and the analgesic effect was determined in the hot plate test after intravenous injection into mice.

Figure 5:
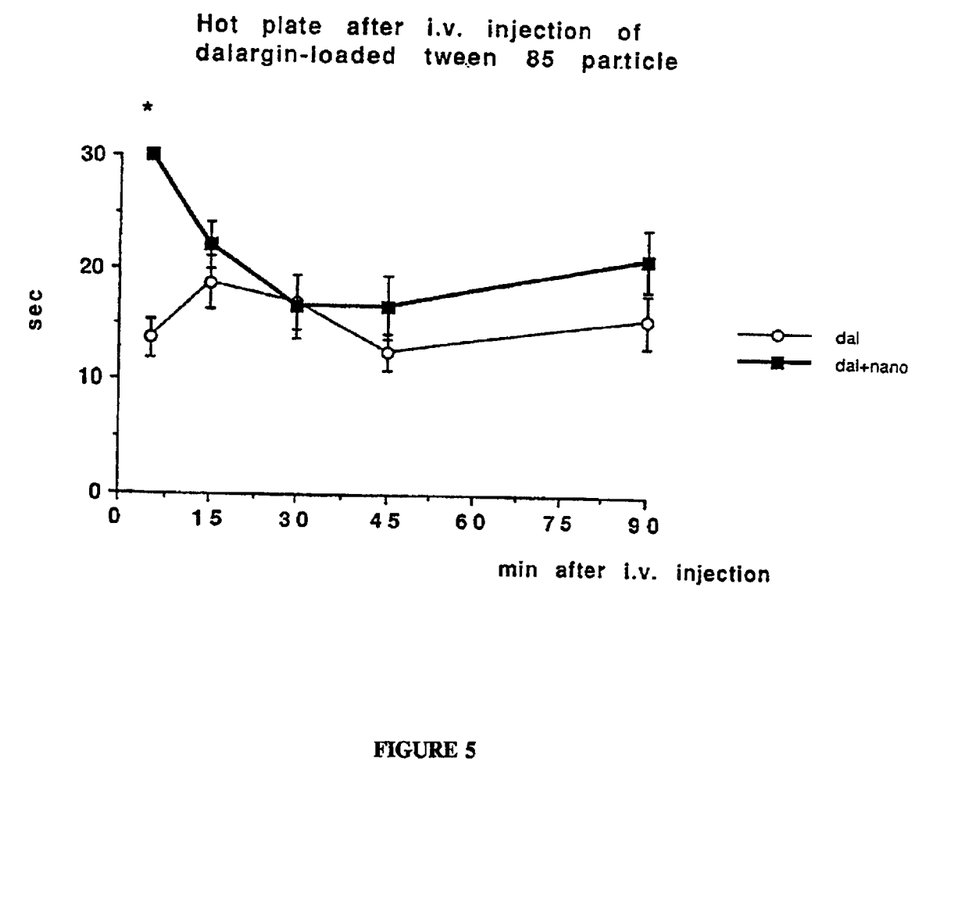
FIG. 5 illustrates the analgesic effect as demonstrated with the hot plate test after intravenous application of dalargin (10 mg/kg). Dalargin was given either in solution, or after sorptive binding to nanoparticles that were stabilized with Dextran 12.000.

It could be shown that these dalargin-loaded nanoparticles are also effective without that a coating of a surfactant is applied (FIG. 5).

What is claimed is:

1. A method for preparing a nanoparticle formulation for administering one or more physiologically effective substances to the central nervous system comprising;

a) providing nanoparticles consisting essentially of a polymeric material comprising one or more monomeric or oligomeric precursors polymerized in the presence of one or more stablilizers, and loaded with one or more physiologically effective substances, wherein the stabilizers are selected from the group consisting of polysorbate 85, dextran 12,000 and mixtures thereof; and optionally b) loading an effective amount of one or more physiologically effective substances to be delivered to the central nervous system of the patient into or onto the nanoparticles or both; and optionally c) providing the nanoparticles in a medium allowing the transport of the nanoparticles to the central nervous system of a patient.

* * * * *